US008969639B2

(12) United States Patent
Xu et al.

(10) Patent No.: US 8,969,639 B2
(45) Date of Patent: Mar. 3, 2015

(54) DEHYDROGENATION PROCESS

(75) Inventors: Teng Xu, Houston, TX (US); Stuart L. Soled, Pittstown, NJ (US); Edward A. Lemon, Jr., Easton, PA (US); Christine E. Kliewer, Clinton, NJ (US); Tan-Jen Chen, Kingwood, TX (US); Joseph E. Baumgartner, Califon, NJ (US); Sabato Miseo, Pittstown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/512,625

(22) PCT Filed: Dec. 17, 2010

(86) PCT No.: PCT/US2010/061016
§ 371 (c)(1),
(2), (4) Date: Jun. 26, 2012

(87) PCT Pub. No.: WO2011/096994
PCT Pub. Date: Aug. 11, 2011

(65) Prior Publication Data
US 2012/0271077 A1 Oct. 25, 2012

Related U.S. Application Data

(60) Provisional application No. 61/301,794, filed on Feb. 5, 2010, provisional application No. 61/334,775, filed on May 14, 2010.

(51) Int. Cl.
*C07C 5/10* (2006.01)
*B01J 37/02* (2006.01)
*B01J 23/40* (2006.01)
*C07C 5/367* (2006.01)
*C07C 5/373* (2006.01)
*C07C 13/19* (2006.01)

(52) U.S. Cl.
CPC .............. *B01J 37/0203* (2013.01); *B01J 23/40* (2013.01); *C07C 5/367* (2013.01); *C07C 5/373* (2013.01); *C07C 13/19* (2013.01); *C07C 2523/42* (2013.01)

USPC ............................ 585/252; 585/430; 585/434

(58) Field of Classification Search
USPC ......................................................... 585/252
See application file for complete search history.

(56) References Cited

U.S. PATENT DOCUMENTS 3,308,069 A   3/1967  Wadlinger et al.
3,534,110 A  10/1970  Juguin et al.

(Continued)

FOREIGN PATENT DOCUMENTS

GB         514587      11/1939
JP       58-067636      4/1983
WO     2009/131769     10/2009

OTHER PUBLICATIONS

Du et al., "The Chemistry of Selective Ring-Opening Catalysts", Applied Catalysis A: General, 2005, vol. 294, No. 1, pp. 1-21.

(Continued)

*Primary Examiner* — In Suk Bullock
*Assistant Examiner* — Youngsul Jeong
(74) *Attorney, Agent, or Firm* — Jamie L. Sullivan; Siwen Chen

(57) ABSTRACT

In a dehydrogenation process a hydrocarbon stream comprising at least one non-aromatic six-membered ring compound and at least one five-membered ring compound is contacted with a dehydrogenation catalyst produced by a method comprising treating the support with a liquid composition comprising the dehydrogenation component or a precursor thereof and at least one organic dispersant selected from an amino alcohol and an amino acid. The contacting is conducted under conditions effective to convert at least a portion of the at least one non-aromatic six-membered ring compound in the hydrocarbon stream to benzene and to convert at least a portion of the at least one five-membered ring compound in the hydrocarbon stream to paraffins.

24 Claims, 2 Drawing Sheets

(56) References Cited

U.S. PATENT DOCUMENTS

| | | |
|---|---|---|
| 3,761,428 A | 9/1973 | Sugier et al. |
| 3,856,661 A | 12/1974 | Sugier et al. |
| RE28,341 E | 2/1975 | Wadlinger et al. |
| 3,962,362 A | 6/1976 | Suggitt |
| 4,094,918 A | 6/1978 | Murtha et al. |
| 4,122,125 A | 10/1978 | Murtha et al. |
| 4,147,726 A | 4/1979 | Wu |
| 4,177,165 A | 12/1979 | Murtha et al. |
| 4,206,082 A | 6/1980 | Murtha et al. |
| 4,501,926 A | 2/1985 | LaPierre et al. |
| 4,891,458 A | 1/1990 | Innes et al. |
| 4,933,507 A | 6/1990 | Inoki et al. |
| 5,053,571 A | 10/1991 | Makkee |
| 5,811,624 A | 9/1998 | Hantzer et al. |
| 5,906,729 A | 5/1999 | Chou |
| 6,037,513 A | 3/2000 | Chang et al. |
| 7,538,066 B2 | 5/2009 | Soled et al. |
| 7,563,358 B2 | 7/2009 | Stavens et al. |
| 7,579,511 B1 * | 8/2009 | Dakka et al. ............... 585/316 |
| 7,605,107 B2 * | 10/2009 | Soled et al. ............... 502/216 |
| 2006/0166809 A1 | 7/2006 | Malek et al. |

OTHER PUBLICATIONS

Galperin et al., "*Effect of Support Acid-Basic Properties on Activity and Selectivity of Pt Catalysts in Reaction of Methylcyclopentane Ring Opening*", Applied Catalysis A: General, 2003, vol. 239, No. 1-2, pp. 297-304.

Gault, "*Mechanisma of Skeletal Isomerization of Hydrocarbons on Metals*", Advances in Catalysis, 1981, vol. 30, pp. 1-95.

Gonzales-Cortes et al., "*Tuning the Ring-Opening Reaction of 1,3-dimethylcyclohexane with the Addition of Potassium Over Ir-Containing Catalysts*", Chemical Engineering Journal, 2008, vol. 139, pp. 147-156.

Saito, Y., et al."*Performance of activity test on supported Pd catalysts for dehydrogenation of cyclohexanone to phenol (effect of supports on activity)*", Ibaraki Kogyo Koto Senmon Gakko Kenkyu Iho (1995), vol. 30, pp. 39-46—English Abstract Only.

Smirniotis et al., "*Comparison Between Zeolite $\beta$ and $\gamma$-$Al_2O_3$ Supported Pt for Reforming Reactions*", Journal of Catalysis, 1993, vol. 140, pp. 526-542.

Smirniotis et al., "*Increased Aromatization in the Reforming of Mixtures of N-Hexane, Methylcyclopentane and Methylcyclohexane Over Composites of Pt/BaKL Zeolite with Pt/beta or Pt/USY Zeolites*", Applied Catalysis A: General, 1995, vol. 123, No. 1, pp. 59-88.

Soled et al., "*Supported Metal Catalysts: Some Interesting New Leads in an Old Field*", Scientific Bases for the Preparation of Heterogeneous Catalysts, 2006, vol. 162, pp. 103-110.

Koshel et al. "*A Commercial Synthesis of Phenylcyclohexane ((PHCH)) by the Hydrodimerization of Benzene*", Neftekhimiya, 1977, vol. 17, pp. 705-709.

* cited by examiner

US 8,969,639 B2

DEHYDROGENATION PROCESS

PRIORITY CLAIM

This application is a National Stage Application of International Application No. PCT/US2010/061016 filed Dec. 17, 2010, which claims priority to U.S. Provisional Application Ser. No. 61/301,794, filed Feb. 5, 2010; and U.S. Provisional Application Ser. No. 61/334,775, filed May 14, 2010, the disclosures of which are fully incorporated herein by their reference.

CROSS REFERENCE TO RELATED APPLICATIONS

This patent application is related to U.S. Provisional Application Ser. No. 61/334,767, filed May 14, 2010; U.S. Provisional Application Ser. No. 61/334,781, filed May 14, 2010; U.S. Provisional Application Ser. No. 61/334,784, filed May 14, 2010; and U.S. Provisional Application Ser. No. 61/334,787, filed May 14, 2010, the disclosures of which are fully incorporated herein by their reference.

FIELD

The present invention relates to a process for dehydrogenating hydrocarbon streams and in particular the C6-rich streams produced in the hydroalkylation of benzene to produce cyclohexylbenzene.

BACKGROUND

Various dehydrogenation processes have been proposed to dehydrogenate non-aromatic six membered ring compounds. These dehydrogenation processes are typically used to convert non-aromatic compounds such as cyclohexane into aromatic compounds such as benzene wherein the aromatic compound produced may be used as a raw material in a subsequent process. Alternatively, the aromatic compound produced may be used as a raw material in the same process which produced the non-aromatic compound to be dehydrogenated. For example, the dehydrogenation of cyclohexane to benzene can be important in the hydroalkylation process for producing cyclohexylbenzene as illustrated below.

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low particularly at economically viable benzene conversion rates and that large quantities of unwanted by-products, particularly cyclohexane and methylcyclopentane, were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a hydrogen to benzene molar ratio of about 0.01 to 100 and a weight hourly space velocity (WHSV) of about 0.01 to 100 hr$^{-1}$. The '513 patent discloses that the resultant cyclohexylbenzene can then be oxidized to the corresponding hydroperoxide and the peroxide decomposed to the desired phenol and cyclohexanone.

Not only does production of impurities such as cyclohexane and methylcyclopentane represent loss of valuable benzene feed, but also overall benzene conversion rates are typically only 40 to 60 wt % so that recycle of unreacted benzene is essential. Unless removed, these impurities will tend to build up in the recycle stream thereby displacing benzene and increasing the production of undesirable by-products. Thus a significant problem facing the commercial application of cyclohexylbenzene as a phenol precursor is removing the cyclohexane and methylcyclopentane impurities in the benzene recycle streams.

One solution to this problem is proposed in U.S. Pat. No. 7,579,511 which describes a process for making cyclohexylbenzene in which benzene undergoes hydroalkylation in the presence of a first catalyst to form a first effluent stream containing cyclohexylbenzene, cyclohexane, methyl cyclopentane, and unreacted benzene. The first effluent stream is then separated into a cyclohexane/methylcyclopentane-rich stream, a benzene-rich stream, and a cyclohexylbenzene-rich stream and the cyclohexane/methylcyclopentane-rich stream is contacted with a second, low acidity, dehydrogenation catalyst to convert at least a portion of the cyclohexane to benzene and at least a portion of the methylcyclopentane to linear and/or branched paraffins and form a second effluent stream. The benzene-rich stream and the second effluent stream can then be recycled to the hydroalkylation step. However, one problem with this process is that cyclohexane and methylcyclopentane have similar boiling points to that of benzene so that their separation by conventional distillation is difficult.

Another solution is proposed in International Patent Publication No. WO2009/131769, in which benzene undergoes hydroalkylation in the presence of a first catalyst to produce a first effluent stream containing cyclohexylbenzene, cyclohexane, and unreacted benzene. The first effluent stream is then divided into a cyclohexylbenzene-rich stream and a C$_6$ product stream comprising cyclohexane and benzene. At least part of said C$_6$ product stream is then contacted with a second catalyst under dehydrogenation conditions to convert at least part of the cyclohexane to benzene and produce a second effluent stream which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group VIII metal on a porous inorganic support such as aluminum oxide, silicon oxide, titanium oxide, zirconium oxide, activated carbon and combinations thereof. However, in practice, such a dehydrogenation catalyst has only limited activity for the conversion of methylcyclopentane and in some instances can undergo rapid aging. There is therefore a need for an improved catalyst for removing cyclohexane and methylcyclopentane from the benzene recycle streams employed in benzene hydroalkylation processes.

According to the present invention, it has now been found that, by adding an amino acid or amino alcohol to the liquid vehicle used to deposit the dehydrogenation metal onto the support, the dispersion of the dehydrogenation metal on the support can be improved resulting in a more effective catalyst for the dehydrogenation of cyclohexane to benzene and methylcyclopentane to paraffins in benzene-containing and other hydrocarbon streams catalysts. These catalyst exhibit high activity for the conversion of both five- and six-membered non-aromatic rings and yet have a relatively low aging rate.

SUMMARY

In one aspect, the invention resides in a dehydrogenation process comprising:

(a) providing a hydrocarbon stream comprising at least one non-aromatic six-membered ring compound and at least one five-membered ring compound; and (b) producing a dehydrogenation reaction product stream comprising the step of contacting at least a portion of said hydrocarbon stream with a dehydrogenation catalyst comprising a support and a metal component and said contacting being conducted under conditions effective to convert at least a portion of the at least one non-aromatic six-membered ring compound in said hydrocarbon stream to benzene and to convert at least a portion of the at least one five-membered ring compound in said hydrocarbon stream to at least one paraffin, wherein the dehydrogenation catalyst is produced by a method comprising treating the support with a liquid composition comprising the metal component or a precursor thereof and at least one organic dispersant selected from an amino alcohol and an amino acid.

Conveniently, the support is selected from the group consisting of silica, a silicate, an aluminosilicate, carbon, and carbon nanotubes.

Conveniently, the metal component is selected from Groups 6 to 10 of the Periodic Table of Elements, such as platinum and palladium.

In one embodiment, said at least one organic dispersant comprises an amino acid, especially arginine.

Conveniently, said dehydrogenation catalyst has an alpha value from about 0 to about 20, about 0 to about 5, and about 0 to about 1.

Conveniently, said conditions in the contacting (b) comprise a temperature between about 200° C. and about 550° C. and a pressure between about 100 and about 7,000 kPaa.

In one embodiment, said hydrocarbon stream is a $C_6$ hydrocarbon-rich stream containing benzene, cyclohexane and methylcyclopentane.

Conveniently, said $C_6$ hydrocarbon-rich stream is produced by:

(c) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene; and (d) separating at least a portion of the hydroalkylation reaction product stream into said $C_6$ hydrocarbon-rich stream and a cyclohexylbenzene-rich stream.

In another aspect, the invention resides in a process for producing cyclohexylbenzene, the process comprising:

(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;

(b) separating at least a portion of the hydroalkylation reaction product stream into (i) a $C_6$-rich stream comprising benzene, cyclohexane, and methylcyclopentane and (ii) a cyclohexylbenzene-rich stream;

(c) contacting at least a portion of said $C_6$-rich stream with a dehydrogenation catalyst comprising at least one dehydrogenation metal or compound thereof and at least one molecular sieve, said contacting being conducted under conditions effective to convert at least a portion of the cyclohexane to benzene and at least a portion of the methylcyclopentane to at least one paraffin and form a dehydrogenation reaction product stream;

(d) separating at least a portion of said dehydrogenation reaction product stream produced into a $C_6$ recycle stream and a paraffins-rich stream;

(e) recycling at least a portion of the said $C_6$ recycle stream to (a); and (f) recovering cyclohexylbenzene from said cyclohexylbenzene-rich stream.

Conveniently, said hydroalkylation conditions include a temperature between about 100° C. and about 400° C. and a pressure between about 100 and about 7,000 kPa.

Conveniently, wherein the hydrogen and benzene are fed to said contacting (a) in a molar ratio of hydrogen to benzene of between about 0.15:1 and about 15:1.

Conveniently, hydrogen and benzene are fed to said contacting (a) in a molar ratio of hydrogen to benzene of between about 0.15:1 and about 15:1.

Conveniently, said hydroalkylation catalyst comprises a molecular sieve of the MCM-22 family and a hydrogenation metal.

DETAILED DESCRIPTION

Figures 1A, 1B:
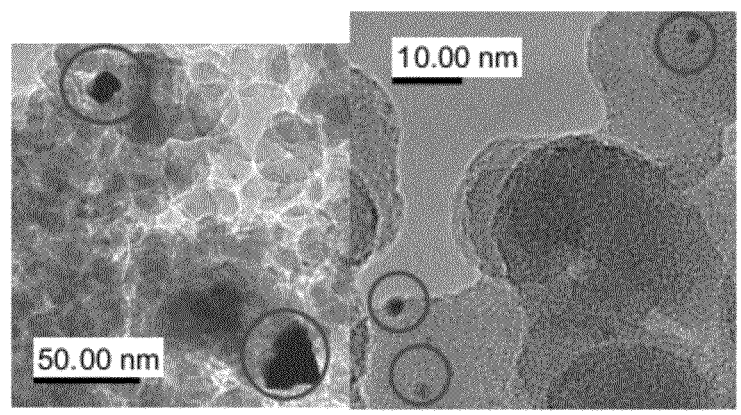
FIGS. 1(a) and (b) are transmission electron micrographs (TEM) of the 1% Pt/$SiO_2$ catalyst of Example 1 at on-screen magnifications of 57,000 times and 110,000 times respectively.

Described herein is a process for dehydrogenating a hydrocarbon stream comprising at least one non-aromatic six-membered ring compound and at least one non-aromatic five-membered ring compound and optionally at least one aromatic compound, such as benzene. The process comprises contacting at least a portion of the hydrocarbon stream with a dehydrogenation catalyst under conditions effective to convert at least a portion of the at least one non-aromatic six-membered ring compound in the hydrocarbon stream to benzene and to convert at least a portion of the at least one five-membered ring compound in the hydrocarbon stream to at least one paraffin and form a dehydrogenation reaction product stream.

In one embodiment, the hydrocarbon stream comprises at least at least 10 wt % benzene, at least 20 wt % benzene, at least 30 wt % benzene, at least 40 wt % benzene, 50 wt % benzene, at least 60 wt % benzene, at least 70 wt % benzene, and at least 80 wt % benzene. In another embodiment, the hydrocarbon stream comprises at least 1 wt % cyclohexane, at least 5 wt % cyclohexane, at least 10 wt % cyclohexane, and at least 20 wt % cyclohexane. In still another embodiment, the hydrocarbon stream comprises at least 0.05 wt % methylcyclopentane, at least 0.1 wt % methylcyclopentane, and 0.2 wt % methylcyclopentane.

The dehydrogenation catalyst employed in the present process comprises at least one dehydrogenation metal or a compound thereof and at least one molecular sieve.

Dehydrogenation Catalyst and Process

The dehydrogenation catalyst comprises a support, typically formed of silica, a silicate, an aluminosilicate, carbon, or carbon nanotubes, on which is deposited a dehydrogenation component, typically comprising at least one metal component selected from Groups 6 to 10 of the Periodic Table of Elements.

In one embodiment, dehydrogenation component comprises at least one metal component selected from Groups 6 to 10 of the Periodic Table of Elements, such as platinum and palladium such that the dehydrogenation component may comprise any combination or mixture of metal components selected from Groups 6 to 10 of the Periodic Table of Elements. In another embodiment, the dehydrogenation component comprises at least one metal component selected from Group 10 of the Periodic Table of Elements. In other embodiments, the dehydrogenation component consists of one metal component selected from Group 6 to Group 10 of the Periodic Table of Elements; one metal component selected from Group 10 of the Periodic Table of Elements; or one metal component selected from palladium and platinum. In still another embodiment, the catalyst consists of a support and a dehydrogenation component selected from Group 10 of the Periodic Table of Elements. Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In one embodiment, the dehydrogenation catalyst comprises a silica support having pore volumes and median pore diameters determined by the method of mercury intrusion porosimetry described by ASTM Standard Test D4284. The silica support may have surface areas as measured by ASTM D3663. In one embodiment, the pore volumes are in the range of from about 0.2 cc/gram to about 3.0 cc/gram. The median pore diameters are in the range from about 10 angstroms to about 2000 angstroms, or from about 20 angstroms to about 500 angstroms; and the surface areas (m2/gram) are in the range from about 10 m2/gram to about 1000 m2/gram, or from about 20 m2/gram to about 500 m2/gram. The support may or may not comprise a binder.

In one embodiment, the catalyst further contains an inorganic base component comprising a metal component selected from an alkali metal, an alkaline earth metal, an alkali metal compound, and an alkaline earth metal compound, especially potassium or a potassium compound. In another embodiment, the catalyst further contains an inorganic base component comprising a metal component selected from Group 1 and Group 2 of the Periodic Table of Elements. Typically, the inorganic base component is present in an amount between about 0.1 wt % and about 5 wt % of the catalyst.

The term "metal component" is used herein to include a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

The dehydrogenation catalyst may be used to dehydrogenate any dehydrogenatable hydrocarbon such as an alicyclic compound. "Dehydrogenatable hydrocarbon" refers to all classes of hydrocarbons containing saturated carbon bonds which have the potential for forming one or more unsaturated bonds through the process of dehydrogenation. "Alicyclic compounds" refers to saturated or unsaturated non-aromatic hydrocarbon ring systems containing from three to twenty ring carbon atoms wherein the hydrocarbon ring system may also have a side-chain or a functional group attached directly to or bound within the ring. Examples of alicyclic compounds include, without limitation, cyclopropane, cyclopentane, methyl cyclopentane, cyclobutane, cyclopentene, cyclodecane, cyclohexane, methylcyclohexane, cyclododecane, and six carbon ring alicyclic compounds such as cyclohexane. Other examples of alicyclic compounds include without limitation alicyclic ketones such as cyclohexanone and alicyclic alcohols such as cyclohexanol.

In one embodiment, at least a portion of the six carbon ring alicyclic compounds are dehydrogenated (or converted) to aromatic compounds such as benzene and phenol. For example, at least a portion of cyclohexanone may be dehydrogenated to phenol and at least a portion of cyclohexane may be dehydrogenated to benzene.

In another embodiment, at least a portion of the alicyclic compounds are (i) dehydrogenated to unsaturated compounds; (ii) rearranged to form other alicyclic compounds; or (iii) fragment to lighter hydrocarbons.

The present dehydrogenation catalyst is prepared by initially treating the support, normally by impregnation, with a liquid composition comprising the dehydrogenation component or a precursor thereof, the optional inorganic base component and at least one organic dispersant selected from an amino alcohol and an amino acid. The organic dispersant may be dispersed in a liquid carrier. The liquid carrier is generally water. Examples of amino alcohols include wherein the amino alcohol is selected from the group consisting of methanolamine, dimethanolamine, tri-methanolamine, ethanolamine, di-ethanolamine, triethanolamine, butanolamine, dibutanolamine, tributanolamine, propanolamine, dipropanaolamine, tripropanolamine, N,N,-dialkyl-ethanolamines, N-alkyl-diethanolamines, N-alkyl-ethanolamines, N,N,-dialkyl-propanolamines, N-alkyl-dipropanolamines, N-alkyl-propanolamines, N,N,-dialkyl-propanolamines, N-alkyl-dipropanolamines, N-alkyl-propanolamines, N,N,-dialkyl-propanolamines, N-alkyl-dipropanolamines, N-alkyl-propanolamines, N,N,-dialkyl-butonolamines, N-alkyl-dibutanolamines, N-alkyl-butanolamines, N,N,-dialkyl-butanolamines, N-alkyl-dibutanolamines, N-alkyl-butanolamines, N,N,-dialkyl-hexanolamines, N-alkyl-dihexanolamines, N-alkyl-hexanolamines, N,N,-dialkyl-hexanolamines, N-alkyl-dihexanolamines, N-alkyl-hexanolamines, N,N,-dialkyl-heptanolamines, N-alkyl-diheptanolamines, N-alkyl-heptanolamines, N,N,-dialkyl-heptanolamines, N-alkyl-diheptanolamines, N-alkyl-heptanolamines Examples of amino acids include alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, with arginine being preferred.

Generally, the organic dispersant is present in the liquid composition in an amount between about 1 wt % and about 50 wt % based on the weight of the support, preferably in an amount between about 1 wt % and 20 wt %, more preferably in an amount between about 2 wt % to 15 wt % and 5 wt % to 10 wt %. In one embodiment, after treatment with the liquid composition, the support is dried to remove the liquid carrier and is then heated in an oxidizing atmosphere, generally in air, under conditions to decompose substantially all of said organic dispersant. "Decompose substantially all of said organic dispersant" generally means that any remaining organic dispersant left on the support will not materially affect the catalyst dehydrogenation activity. In another embodiment, after treatment with the liquid composition, the support is dried to remove the liquid carrier and is then heated in an oxidizing atmosphere, generally in air, under conditions to decompose essentially all of said organic dispersant. "Decompose essentially all of said organic dispersant" generally means that the organic dispersant cannot be detected on the support by infrared spectroscopy. Suitable conditions for removing the dispersant include a temperature of about 100° C. to about 600° C. for a time of about 0.5 to about 50 hours. The catalyst may then be heated in a reducing atmosphere, such as hydrogen, at a temperature of about 50° C. to about 500° C. for a time of about 0.5 to about 10 hours to reduce the dehydrogenation component.

It is found that adding the organic dispersant to the liquid composition used to deposit the dehydrogenation metal on the support results in a catalyst with improved metal dispersion measured by oxygen chemisorption, with the catalyst produced by the present method typically exhibiting oxygen chemisorption values greater than about 30% and less than about 90%.

In other embodiments, the catalyst has an oxygen chemisorption of greater than about 30%, greater than about 35%, greater than about 40%, greater than about 45%, greater than about 50%, greater than about 55%, greater than about 60%, greater than about 65%, greater than about 70%.

In one embodiment, the Dsv (surface-volume-averaged diameter) of the dehydrogenation component is less than 5 nm as measured by transmission electron micrograph (TEM). Preferably, the Dsv of the dehydrogenation component is from 0.1 nm to 5 nm. In other embodiments, the Dsv lower limit may be 0.1 nm, 0.2 nm, 0.3 nm, 0.4 nm, 0.5 nm, 1 nm, 1.2 nm. 1.5 nm, 1.7 nm, and 2.0 nm; and the upper limit Dsv may be 3 nm, 3.2 nm, 3.5 nm, 3.7 nm, 4.0 nm, 4.5 nm, and 5 nm with ranges from any lower limit to any upper limit being contemplated.

As used herein, the Dsv (surface-volume-averaged diameter) for the catalysts is measured by collecting about 20 to about 80 random images of a given catalyst with a Philips CM 12 or Philips CM 200 transmission electron microscope operated at 120 kV and 200 kV (or equivalent) at screen magnifications of 57,000 to 110,000. For purposes of the experiments, the data were collected as digital images with a Gatan CCD camera system using Gatan's Digital Micrograph program, v. 2.5. The line drawing tool in the Digital Micrograph program was used to mark the diameter of each imaged metal particle from which a statistically determined Dsv is obtained. To calculate the Dsv, a histogram of the distribution of particle sizes is obtained from the TEM (transmission electron microscope) measurements, and from the histogram the Dsv is obtained by the following equation:

$$Dsv=\{sum(N_iD_i^3)\}/\{sum(N_iD_i^2)\}$$

where $N_i$ is the number of particles with a diameter $D_i$.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [11 kPa to 53 kPa]) is measured at 40° C. with $O_2$ as the adsorbent molecule. Extrapolation of the linear portion of this curve to zero pressure gives the total or combined adsorption uptake.

Suitable conditions for the dehydrogenation comprise a temperature of about 250° C. to about 750° C. and a pressure of about 0.01 atm to about 20 atm (1 kPa to 2000 kPa), such as a temperature of about 300° C. to about 500° C. and a pressure of about 1 atm to about 3 atm (100 kPa to 300 kPa).

The reactor configuration used for the dehydrogenation process generally comprises one or more fixed bed reactors containing a solid catalyst with a dehydrogenation function. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

The dehydrogenation catalyst employed herein has an alpha value from about 0 to less than 20, from about 1 to about 10, such as from about 0 to about 15, and from about 0 to about 1. The alpha value is a measure of the acidic functionality of the catalyst and is described together with details of its measurement in U.S. Pat. No. 4,106,218 and in J. Catalysis, Vol. VI, pp. 278-287 (1966) and reference is made to these for such details. Higher alpha values correspond with a more active cracking catalyst. Where necessary the alpha value of the catalyst can be adjusted by methods known in the art, for example by steaming Preferably, the alpha value is from about 0 to about 200 and from about 0 to about 150. In other embodiments, the alpha value lower limit may be about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, and about 10; and the upper alpha value limit may be about 200, about 175, about 150, about 125, about 100, about 90, about 80, about 70, about 60, about 50, about 40, about 30, about 20, about 10, about 5, about 1.9, about 1.8, about 1.7, about 1.6, about 1.5, about 1.4, about 1.3, about 1.2, about 1.1, about 1, about 0.9, about 0.8, about 0.7, about 0.6, and about 0.5 with ranges from any lower limit to any upper limit being contemplated.

The dehydrogenation process is generally conducted at a temperature between about 200° C. and about 550° C., such as between about 300° C. and about 500° C., a pressure between about 100 and about 7,000 kPaa, such as between about 300 and about 3000 kPaa, a weight hourly space velocity (WHSV) between about 0.2 and about 50 $hr^{-1}$, such as between about 1 and about 20 $hr^{-1}$ and a hydrogen to hydrocarbon feed molar ratio between about 0.1 and about 10, such as between about 1 and about 5.

Although the present process can be used with any hydrocarbon stream comprising at least one non-aromatic six-membered ring compound and at least one non-aromatic five-membered ring compound, the process has particular application as part of an integrated process for the conversion of benzene to phenol. In such an integrated process the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

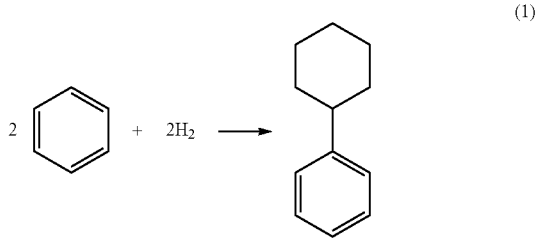 [SMILES: c1ccccc1 ; c1ccc(C2CCCCC2)cc1]

(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is generally a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.5-2 wt %, respectively. The hydroalkylation reaction effluent is therefore fed to a separation system normally comprising at least two distillation towers. Given the similar boiling points of benzene, cyclohexane, and methylcyclopentane, it is difficult to separate these materials by distillation. Thus, in a distillation tower, a $C_6$-rich stream comprising benzene, cyclohexane, and methylcyclopentane is recovered from the hydroalkylation reaction effluent. This $C_6$-rich stream is then subjected to the dehydrogenation process described above such that at least a portion of the cyclohexane in the stream is converted to benzene and at least a portion of the methylcyclopentane is converted to linear and/or branched paraffins, such as 2-methylpentane, 3-methylpentane, n-hexane, and other hydrocarbon components such as isohexane, $C_5$ aliphatics, and $C_1$ to $C_4$ aliphatics. The dehydrogenation product stream is then fed to a further separation system, typically a further distillation tower, to divide the dehydrogenation product stream into a $C_6$ recycle stream and a paraffin-rich stream comprising 2-methylpentane, 3-methylpentane, and other $C_1$ to $C_6$ paraffins. The $C_6$ recycle stream can then be recycled to the hydroalkylation step, while the paraffinic stream can be used as a fuel for the process.

After separation of the $C_6$-rich stream, the remainder of hydroalkylation reaction effluent is fed a second distillation tower to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore zeolite has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1. The transalkylation reaction effluent can then be returned to the second distillation tower to recover the additional monocyclohexylbenzene product produced in the transalkylation reaction.

After separation in the second distillation tower, the cyclohexylbenzene is converted into phenol by a process similar to the Hock process. In this process, the cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst can be used in this reaction such as the catalyst or a variation of the dehydrogenation catalyst described herein.

Other suitable dehydrogenation catalysts include a dehydrogenation catalyst comprising (i) a dehydrogenation component comprising a Group 6 to Group 10 metal component and (ii) a metal promoter comprising a Group 1 or Group 2 metal component. The dehydrogenation catalyst may be produced by initially treating the support, such as by impregnation, with a solution of the metal promoter, such as an aqueous solution of potassium carbonate. After drying, the treated support is calcined, normally in an oxygen-containing atmosphere, such as air, at a temperature of about 100° C. to about 700° C. for a time of about 0.5 to about 50 hours. The calcined support is then treated, again typically by impregnation, with a solution of the dehydrogenation component or a precursor thereof. Optionally, the dehydrogenation component may be impregnated into the support with the aid of at least one organic dispersant. The organic dispersant may help to increase the metal dispersion of the first component. The at least one organic dispersant may be used to increase the metal dispersion of the dehydrogenation component with or without the impregnation of the first component into the support. The at least one organic dispersant is selected from an amino alcohol and an amino acid, such as arginine. Generally, the organic dispersant is present in an amount between about 1 and about 20 wt % of the solution.

Suitable conditions for the dehydrogenation step comprise a temperature of about 250° C. to about 500° C. and a pressure of about 0.01 atm to about 20 atm (1 kPa to 2000 kPa), such as a temperature of about 300° C. to about 450° C. and a pressure of about 1 atm to about 3 atm (100 kPa to 300 kPa).

Provided are one or more embodiments:

A. A dehydrogenation process comprising:
 (a) providing a hydrocarbon stream comprising at least one non-aromatic six-membered ring compound and at least one five-membered ring compound; and
 (b) producing a dehydrogenation reaction product stream comprising the step of contacting at least a portion of the hydrocarbon stream with a dehydrogenation catalyst comprising a support and a metal component under conditions effective to convert at least a portion of the at least one non-aromatic six-membered ring compound to benzene and to convert at least a portion of the at least one five-membered ring compound to at least one paraffin,
 wherein the dehydrogenation catalyst is produced by a method comprising treating the support with a liquid composition comprising the metal component or a precursor thereof and at least one organic dispersant selected from an amino alcohol and an amino acid.

B. The process of embodiment A, wherein the dehydrogenation catalyst has an alpha value from about 0 to about 20.

C. The process of any one of embodiments A to B, wherein the dehydrogenation catalyst has an alpha value from about 0 to about 5.

D. The process of any one of embodiments A to C, wherein the dehydrogenation catalyst has an alpha value from about 0 to about 1.

E. The process of any one of embodiments A to D, wherein the dispersant is present in the liquid composition in an amount between about 1 wt % and about 20 wt % based on the weight of the support.

F. The process of any one of embodiments A to E, wherein the support is at least one material selected from silica, a silicate, an aluminosilicate, carbon, and carbon nanotubes.

G. The process of any one of embodiments A to F, wherein the metal component comprises at least one metal component selected from Groups 6 to 10 of the Periodic Table of Elements.

H. The process of any one of embodiments A to G, wherein the dehydrogenation component comprises at least one metal component selected from platinum and palladium.

I. The process of any one of embodiments A to H, wherein the at least one organic dispersant comprises an amino acid.

J. The process of any one of embodiments A to I, wherein the at least one organic dispersant comprises arginine.

K. The process of any one of embodiments A to J, wherein the at least one organic dispersant comprises an amino alcohol.

L. The process of any one of embodiments A to K, wherein the catalyst has an oxygen chemisorption of at least 30%.

M. The process of any one of embodiments A to L, wherein the catalyst has an oxygen chemisorption of at least 40%.

N. The process of any one of embodiments A to M wherein the catalyst has an oxygen chemisorption of at least 50%.

O. The process of any one of embodiments A to N, wherein the metal component has a Dsv of less than 5 nm as measured by TEM.

P. The process of any one of embodiments A to O, wherein the method of producing the catalyst further comprises heating the treated support in an oxidizing atmosphere under conditions to decompose substantially all of the organic dispersant.

Q. The process of any one of embodiments A to P, wherein the method of producing the catalyst further comprises heating the treated support in an oxidizing atmosphere under conditions to decompose essentially all of the organic dispersant.

R. The process of any one of embodiments A to Q, wherein the conditions in the contacting step (b) comprise a temperature between about 200° C. and about 550° C. and a pressure between about 100 and about 7,000 kPaa.

S. The process of any one of embodiments A to R, wherein the hydrocarbon stream is a $C_6$-rich stream comprising at least 50 wt % benzene, at least 5 wt % cyclohexane, and at least 0.1 wt % methylcyclopentane.

T. The process of embodiment S, wherein the $C_6$-rich stream is produced by:
(c) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene; and
(d) separating at least a portion of the hydroalkylation reaction product stream into the $C_6$-rich stream and a cyclohexylbenzene-rich stream.

U. The process of embodiment T, and further comprising:
(e) separating at least a portion of the dehydrogenation reaction product stream produced in the contacting step (b) into a benzene recycle stream and a paraffin-rich stream comprising 2-methylpentane and 3-methylpentane; and
(f) recycling at least a portion of the benzene recycle stream to the contacting step (c).

V. A process for producing cyclohexylbenzene, the process comprising:
(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;
(b) separating at least a portion of the hydroalkylation reaction product stream into (i) a $C_6$-rich stream comprising benzene, cyclohexane, and methylcyclopentane and (ii) a cyclohexylbenzene-rich stream;
(c) producing a dehydrogenation reaction product stream comprising the step of contacting at least a portion of the $C_6$-rich stream with a dehydrogenation catalyst comprising a metal component and a support and the contacting being conducted under conditions effective to convert at least a portion of the cyclohexane to benzene and at least a portion of the methylcyclopentane to at least one paraffin wherein the dehydrogenation catalyst is produced by a method comprising treating the support with a liquid composition comprising the metal component or a precursor thereof and at least one organic dispersant selected from an amino alcohol and an amino acid;
(d) separating at least a portion of the dehydrogenation reaction product stream produced into a benzene recycle stream and a paraffins-rich stream comprising 2-methylpentane and 3-methylpentane;
(e) recycling at least a portion of the benzene recycle stream to the contacting step (a); and
(f) recovering cyclohexylbenzene from the cyclohexylbenzene-rich stream.

W. The process of embodiment V, wherein the hydroalkylation conditions in the contacting
(a) include a temperature between about 100° C. and about 400° C. and a pressure between about 100 and about 7,000 kPa.

X. The process of any one of embodiments V to W, wherein the hydrogen and benzene are fed to the contacting (a) in a molar ratio of hydrogen to benzene of between about 0.15:1 and about 15:1.

Y. The process of any one of embodiments V to X, wherein the hydroalkylation catalyst comprises a molecular sieve of the MCM-22 family and a hydrogenation metal.

When a stream is described as being "rich" in a specified species, it is meant that the specified species in that stream is enriched relative to other species in the same stream or composition on a weight percentage basis. For illustration purposes only, a cyclohexylbenzene-rich stream will have a cyclohexylbenzene wt % greater than any other species or component in that same stream. A "$C_6$" species generally means any species containing 6 carbon atoms.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [10.7 to 53.3 kPa]) is measured at 40° C. with $O_2$ as the adsorbent molecule. Extrapolation of the linear portion of this curve to zero pressure gives the total or combined adsorption uptake.

The invention will now be more particularly described with reference to the following non-limiting Examples and the accompanying drawings.

Catalyst Preparation

Catalysts were pressed into thin disks using a hydraulic press at a pressure of five metric tons. The thin catalyst disks were crushed and sieved. Catalyst particles between 30 to 40 mesh were collected for catalyst testing. 400 mg of pelletized catalyst was mixed with 3.5 grams 40 mesh quartz chips, and the mixture was packed into a ¼" (6.4 mm) stainless steel reactor. The liquid feed for the reaction was composed of 75 wt % benzene, 20 wt % cyclohexane, and 5 wt % methylcyclopentane (MCP). The liquid feed was delivered using an ISCO pump. The liquid feed was vaporized prior to mixing with $H_2$ feed. The mixed feed was fed into a down flow reactor. The reaction was typically run at 425° C. to 500° C., 50 to 200 psig (345 to 689 KPag) total reactor pressure. The weight hourly space velocity (WHSV) varied from 2.5 to 10 hr−1. The $H_2$/liquid feed molar ratio was varied from 1 to 4.

Prior to the introduction of the feed, the catalyst was pretreated in 100 standard cubic centimeters per minute (sccm) $H_2$ at 100 psig (689 KPag) by ramping reactor temperature from room temperature to 425° C. at 2° C./min. The reactor temperature was held at 425° C. for two (2) hours under the same $H_2$ flow and pressure to allow for reduction of supported catalysts prior to testing.

The effluent from the reactor was sampled using a Valco sampling valve, and the sample was sent to an on-line GC equipped with a FID for analysis. All the hydrocarbons were analyzed and the results were normalized. $H_2$ was not included in the analysis. All the concentrations shown here are in wt %. Cyclohexane conversion and methylcyclopentane conversion were calculated following formula shown below.

Cyclohexane (CH) conversion %=[(CH wt % in feed−CH wt % in effluent)/CH wt % in feed]*100.

Methylcyclopentane (MCP) conversion %=[(MCP wt % in feed−MCP wt % in effluent)/MCP wt % in feed]*100.

Example 1

Preparation of 1 wt % Pt/Silica Catalyst (Catalyst A—Comparative)

11.2 g of tetraamine platinum (II) hydroxide solution containing 4.49 wt % of platinum (Pt) was mixed with 61.1 g of deionized water. The mixture was added dropwise to 50.0 g of silica (Sigma-Aldrich Davison grade 62, 60-200 mesh, 150 angstrom), and the resulting mixture was mixed well. The sample was dried at 120° C. for 2 hours. 10 g of the dried sample was then calcined in an oven by ramping the temperature at a rate of 3° C./minute to 350° C. and maintaining the oven temperature at 350° C. for 16 hrs in 300 sccm of air. The calcined sample was denoted as Catalyst A. The oxygen chemisorption value for catalyst A is 27%.

Example 2

Preparation of 1 wt % Pt/Silica Catalyst with Arginine (Catalyst B—Invention)

2.23 g of tetraamine platinum (II) hydroxide solution containing 4.49 wt % of Pt was mixed with 12.2 g of deionized water. 0.75 g of arginine was added to the mixture. The mixture was then added dropwise to 10.0 g of silica (Sigma-Aldrich Davison grade 62, 60-200 mesh, 150 angstrom), and the resulting mixture was mixed well. The sample was dried at 120° C. for 2 hrs. The dried sample was then calcined in an oven by ramping the temperature at a rate of 3° C./minute to 400° C. and maintaining the oven temperature at 400° C. for 16 hrs in 300 sccm of air. The calcined sample was denoted as Catalyst B. The oxygen chemisorption value for catalyst B is 54%. Note that the Pt dispersion, as measured based on oxygen chemisorption, for catalyst B is 100% greater than that of catalyst A.

Example 3

TEM of 1% Pt/SiO$_2$ (Catalyst A)

FIG. 1 shows two TEM images for the 1% Pt/SiO$_2$ of Example 1. Prior to the TEM studies, the sample was reduced following a similar procedure used for oxygen chemisorption to ensure that Pt particles were properly reduced to metal form. Note the sample has non-uniform Pt particles. Particles as large as about 20 nm and as small as around 2 nm were observed in the sample. The particle Dsv observed was greater than 5 nm.

Example 4

TEM of 1% Pt/SiO$_2$ with Arginine (Catalyst B)

Figure 2:
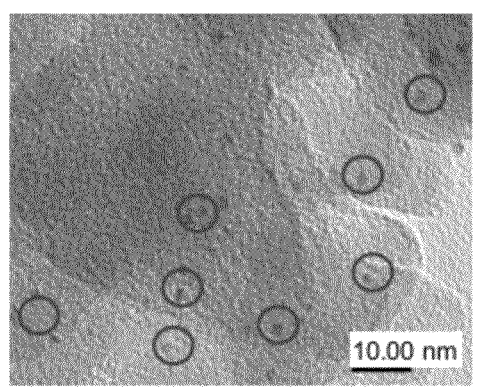
FIG. 2 is a transmission electron micrograph of the 1% Pt/$SiO_2$ catalyst (with arginine dispersion) of Example 2 at an on-screen magnification of 110,000 times.

The same reduction procedure was followed as that used for TEM study of Pt/SiO$_2$ sample. The TEM image is shown in FIG. 2. Note that the Pt particles are relatively uniform, and are much smaller than those shown in FIG. 1. The particle Dsv observed was approximately 2 to 3 nm in the sample.

The results from TEM suggests that the size of Pt particles in catalyst B is much smaller than that of Pt particles in catalyst A, consistent with the fact that Pt dispersion is much higher with catalyst B than with catalyst A as measured by oxygen chemisorption.

Example 5

Performance of Catalyst A for Converting Cyclohexane and Methylcyclopentane

Figure 3:
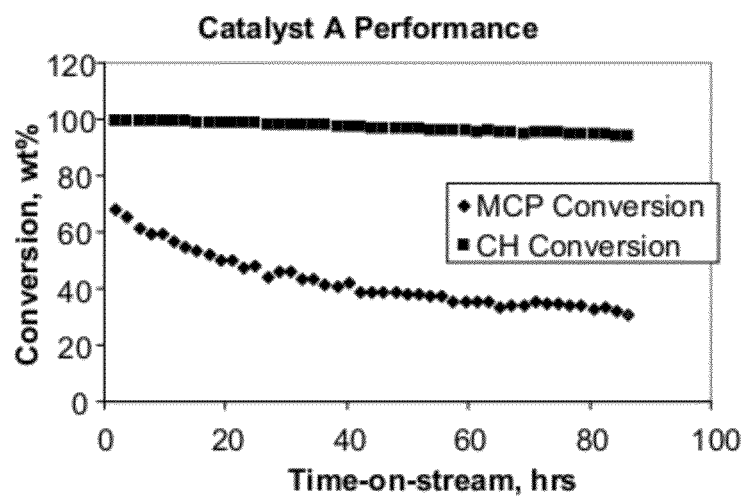
FIG. 3 is a graph that compares cyclohexane conversion and methylcyclopentane conversion against time on stream for the catalyst of Example 1.

FIG. 3 shows the conversion of cyclohexane (CH) and methylcyclopentane on catalyst A at 480 C., 100 psig (689 KPag), 10 WHSV, and a hydrogen to feed molar ratio of 3.5. The feed contained 75 wt % benzene, 20 wt % cyclohexane and 5 wt % methylcyclopentane.

The catalyst was active in converting cyclohexane to benzene. The selectivity for benzene from cyclohexane conversion was close to 100%. The conversion of cyclohexane was close to 100% and declined slowly as time-on-stream increased. The conversion of methylcyclopentane showed faster decline initially. But the conversion of methylcyclopentane seemed to stabilize around 20 to 30%. The main products from methylcyclopentane conversion are hexane, 2-methylpentane, and 3-methylpentane. The latter two compounds can be readily separated from methylcyclopentane (e.g. via conventional distillation).

Example 6

Performance of Catalyst B for Converting Cyclohexane and Methylcyclopentane

Figure 4:
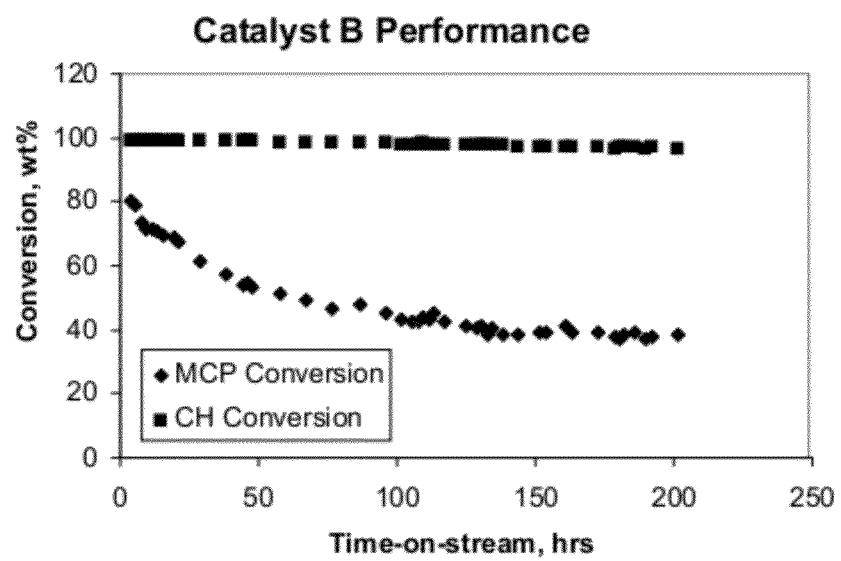
FIG. 4 is a graph that compares cyclohexane conversion and methylcyclopentane conversion against time on stream for the catalyst of Example 2.

FIG. 4 shows the conversion of cyclohexane (CH) and methylcyclopentane on catalyst B at 480 C., 100 psig (689 KPag), 10 WHSV, and a hydrogen to feed molar ratio of 3.5. The feed contained 75 wt % benzene, 20 wt % cyclohexane, and 5 wt % methylcyclopentane.

Note that catalyst B was more active in converting both cyclohexane and methylcyclopentane than catalyst A. Similar to catalyst A, the selectivity for benzene from cyclohexane conversion was close to 100%. The conversion of cyclohexane was close to 100% and remained relatively steady as time-on-stream increased. The conversion of methylcyclopentane on catalyst B was much higher than that of catalyst B. The conversion of methylcyclopentane seemed to stabilize around 40%. The main products from methylcyclopentane conversion are hexane, 2-methylpentane, and 3-methylpentane. The latter two compounds can be readily separated from methylcyclopentane (e.g., via conventional distillation).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A dehydrogenation process comprising:
 (a) providing a hydrocarbon stream comprising at least one non-aromatic six-membered ring compound and at least one five-membered ring compound; and
 (b) producing a dehydrogenation reaction product stream comprising the step of contacting at least a portion of the hydrocarbon stream with a dehydrogenation catalyst comprising a support and a metal component under conditions effective to convert at least a portion of the at least one non-aromatic six-membered ring compound to benzene and to convert at least a portion of the at least one five-membered ring compound to at least one paraffin, wherein the dehydrogenation catalyst is produced by a method comprising treating a support comprising silica with a liquid composition comprising the metal component or a precursor thereof and at least one organic dispersant selected from an amino alcohol and an amino acid.

2. The process of claim 1, wherein the dehydrogenation catalyst has an alpha value from about 0 to about 20.

3. The process of claim 1, wherein the dehydrogenation catalyst has an alpha value from about 0 to about 5.

4. The process of claim 1, wherein the dehydrogenation catalyst has an alpha value from about 0 to about 1.

5. The process of claim 1, wherein the at least one of organic dispersant is present in the liquid composition in an amount between about 1 wt % and about 20 wt % based on the weight of the support.

6. The process of claim 1, wherein the metal component comprises at least one metal component selected from Groups 6 to 10 of the Periodic Table of Elements.

7. The process of claim 1, wherein the dehydrogenation component comprises at least one metal component selected from platinum and palladium.

8. The process of claim 1, wherein the at least one organic dispersant comprises an amino acid.

9. The process of claim 1, wherein the at least one organic dispersant comprises arginine.

10. The process of claim 1, wherein the at least one organic dispersant comprises an amino alcohol.

11. The process of claim 1, wherein the dehydrogenation catalyst has an oxygen chemisorption of at least 30%.

12. The process of claim 1, wherein the dehydrogenation catalyst has an oxygen chemisorption of at least 40%.

13. The process of claim 1, wherein the dehydrogenation catalyst has an oxygen chemisorption of at least 50%.

14. The process of claim 1, wherein the metal component has a surface-volume-averaged diameter (Dsv) of less than 5 nm as measured by TEM.

15. The process of claim 1, wherein the method of producing the catalyst further comprises heating the treated support in an oxidizing atmosphere under conditions to decompose substantially all of the organic dispersant.

16. The process of claim 1, wherein the method of producing the catalyst further comprises heating the treated support in an oxidizing atmosphere under conditions to decompose essentially all of the organic dispersant.

17. The process of claim 1, wherein the conditions in the step of contacting in step (b) comprise a temperature between about 200° C. and about 550° C. and a pressure between about 100 and about 7,000 kPaa.

18. The process of claim 1, wherein the hydrocarbon stream is a $C_6$-rich stream comprising at least 50 wt % benzene, at least 5 wt % cyclohexane, and at least 0.1 wt % methylcyclopentane.

19. The process of claim 18, wherein the $C_6$-rich stream is produced by:
(c) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene; and
(d) separating at least a portion of the hydroalkylation reaction product stream into the C6-rich stream and a cyclohexylbenzene-rich stream.

20. The process of claim 19, and further comprising:
(e) separating at least a portion of the dehydrogenation reaction product stream produced in the step of contacting in step (b) into a benzene recycle stream and a paraffin-rich stream comprising 2-methylpentane and 3-methylpentane; and
(f) recycling at least a portion of the benzene recycle stream to the contacting step (c).

21. A process for producing cyclohexylbenzene, the process comprising:
(a) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;
(b) separating at least a portion of the hydroalkylation reaction product stream into (i) a $C_6$-rich stream comprising benzene, cyclohexane, and methylcyclopentane and (ii) a cyclohexylbenzene-rich stream;
(c) producing a dehydrogenation reaction product stream comprising the step of contacting at least a portion of the $C_6$-rich stream with a dehydrogenation catalyst comprising a metal component and a support and the contacting being conducted under conditions effective to convert at least a portion of the cyclohexane to benzene and at least a portion of the methylcyclopentane to at least one paraffin wherein the dehydrogenation catalyst is produced by a method comprising treating a support comprising silica with a liquid composition comprising the metal component or a precursor thereof and at least one organic dispersant selected from an amino alcohol and an amino acid;
(d) separating at least a portion of the dehydrogenation reaction product stream produced into a benzene recycle stream and a paraffins-rich stream comprising 2-methylpentane and 3-methylpentane;
(e) recycling at least a portion of the benzene recycle stream to the contacting step (a); and
(f) recovering cyclohexylbenzene from the cyclohexylbenzene-rich stream.

22. The process of claim 21, wherein the hydroalkylation conditions in the contacting step (a) include a temperature between about 100° C. and about 400° C. and a pressure between about 100 and about 7,000 kPa.

23. The process of claim 21, wherein the hydrogen and benzene are fed to the contacting step (a) in a molar ratio of hydrogen to benzene of between about 0.15:1 and about 15:1.

24. The process of claim 21, wherein the hydroalkylation catalyst comprises a molecular sieve of the MCM-22 family and a hydrogenation metal.

* * * * *